United States Patent
Majeed et al.

(10) Patent No.: US 10,959,980 B2
(45) Date of Patent: Mar. 30, 2021

(54) BIOACTIVE MOLECULES FROM OROXYLUM INDICUM AND THEIR THERAPEUTIC APPLICATIONS

(71) Applicants: Muhammed Majeed, Bangalore (IN); Kalyanam Nagabhushanam, East Windsor, NJ (US)

(72) Inventors: Muhammed Majeed, Bangalore (IN); Kalyanam Nagabhushanam, East Windsor, NJ (US)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 0 days.

(21) Appl. No.: 16/441,465

(22) Filed: Jun. 14, 2019

(65) Prior Publication Data

US 2019/0381000 A1     Dec. 19, 2019

Related U.S. Application Data

(60) Provisional application No. 62/685,400, filed on Jun. 15, 2018.

(51) Int. Cl.
  *A61K 31/353*   (2006.01)
  *A61P 3/10*     (2006.01)
  *A61K 9/00*     (2006.01)

(52) U.S. Cl.
  CPC .......... *A61K 31/353* (2013.01); *A61K 9/0053* (2013.01); *A61P 3/10* (2018.01)

(58) Field of Classification Search
  CPC ........ A61K 31/353; A61K 9/0053; A61P 3/10
  See application file for complete search history.

(56) References Cited

U.S. PATENT DOCUMENTS

| 10,555,982 | B2 | 2/2020 | Majeed | |
| 2005/0049206 | A1* | 3/2005 | Gong | A61K 31/7048 514/27 |
| 2006/0204596 | A1* | 9/2006 | Jia | A61K 36/48 424/725 |

FOREIGN PATENT DOCUMENTS

WO    WO-2007096739 A2 *    8/2007    ........... A61K 31/352

OTHER PUBLICATIONS

Subramanian et. al., Biochimica et Biophysica Acta, 2012, Elsevier, vol. 1821, pp. 819-825 (Year: 2012).*
Yuan et al. Hypertriglyceridemia: its etiology, effects and treatment, CMAJ 2007;176(8):1113-20.
Medical Officer's Review of New Drug Application 21-071: Rosiglitazone (Avandia). Apr. 19, 1999.
Rosenblit P D, Common medications used by patients with type 2 diabetes mellitus: what are their effects on the lipid profile?, Cardiovasc Diabetol (2016) 15:95.
Buse et al., The effects of oral anti-hyperglycaemic medications on serum lipid profiles in patients with type 2 diabetes, Diabetes, Obesity and Metabolism, 6, 2004, 133-156.
Chen et al., Effects of sulfonylureas on lipids in type 2 diabetes mellitus: a meta-analysis of randomized controlled trials, JEBM 8 (2015) 134-148.
Wulffele et al., The effect of metformin on blood pressure, plasma cholesterol and triglycerides in type 2 diabetes mellitus: a systematic review, J Intern Med, Jul. 2004;256(1):1-14.
Yasuda et al., Effects of rosuvastatin add-on treatment on hyperlipidemia in non-diabetic patients with nephrotic syndrome receiving ethyl icosapentate, Abstracts / Atherosclerosis Supplements 32 (2018) 1-162.

* cited by examiner

*Primary Examiner* — Sarah Pihonak

(57) ABSTRACT

The present invention discloses a composition comprising not less than 10% w/w of oroxylin A, not less than 10% w/w of baicalein and not less than 2% w/w of chrysin for use in the therapeutic management of hypertriglyceridemia, associated with chemotherapy and hyperglycemia.

4 Claims, No Drawings

BIOACTIVE MOLECULES FROM OROXYLUM INDICUM AND THEIR THERAPEUTIC APPLICATIONS

CROSS-REFERENCE TO RELATED PATENT APPLICATIONS

The present invention is non-provisional filing of U.S. provisional patent application No. 62/685,400 filed on 15 Jun. 2018.

BACKGROUND OF THE INVENTION

Field of the Invention

The invention in general relates to compositions for therapeutic management of hypertriglyceridemia. More specifically the present invention relates to therapeutic management of hypertriglyceridemia using a composition comprising oroxylin A, baicalein and chrysin.

Description of Prior Art

Triglycerides are a class of lipid molecules which are stored in the fat cells and released at the time of energy requirement. The body converts the calories into triglycerides and stores in the adipocytes. Hypertriglyceridemia is a clinical condition wherein there is an increase in circulating levels of triglycerides. If the calorie intake exceeds the output, there will be an increase in the levels of triglycerides in blood.

Evidence indicates that elevated triglyceride levels contribute to the increased risk of cardiovascular disease and stroke. Hypertriglyceridemia is associated with an increased risk of acute pancreatitis. The following prior art documents discuss about the causes and effects of hypertriglyceridemia
a) Yuan et al., Hypertriglyceridemia: its etiology, effects and treatment, CMAJ. 2007; 176(8): 1113-1120.
b) Robertson S, Hypertriglyceridemia Cause and Symptoms, https://www.news-medical.net/health/Hypertriglyceridemia-Cause-and-Symptoms.aspx, accessed 10 Jun. 2019
c) John D. Brunzell, Hypertriglyceridemia, N Engl J Med 2007; 357:1009-1017
d) Ceriello et al., Evidence for an Independent and Cumulative Effect of Postprandial Hypertriglyceridemia and Hyperglycemia on Endothelial Dysfunction and Oxidative Stress Generation, Circulation. 2002; 106:1211-1218

Hypertriglyceridemia is often co-morbid with and/or indicate other clinical conditions like diabetes, hyperglycemia, hypothyroidism, metabolic syndrome, obesity, and genetic conditions. It is also present as a side effect of taking certain medications like, chemotherapeutics, diuretics, steroids, beta blockers etc, which can be easily reversed (Triglycerides: Why do they matter?, Mayo Clinic, https://www.mayoclinic.org/diseases-conditions/high-blood-cholesterol/in-depth/triglycerides/art-20048186, accessed 10 Jun. 2019). There are many treatment strategies employed for the management and treatment of hypertriglyceridemia. Natural molecules that can decrease the levels of triglycerides in blood are now being increasingly evaluated. Some of the natural molecules that are reported to reduce triglyceride levels are listed below:
1. Rideout et al., Triglyceride-Lowering Response To Plant Sterol and Stanol Consumption, J AOAC Int. 2015; 98(3): 707-715.
2. Schonewille et al., Serum TG-lowering properties of plant sterols and stanols are associated with decreased hepatic VLDL secretion, J Lipid Res. 2014: 55(12): 2554-2561.
3. Vallianou et al., Camphene, a Plant-Derived Monoterpene, Reduces Plasma Cholesterol and Triglycerides in HyperEpidemic Rats Independently of HMG-CoA Reductase Activity, PLoS ONE 6(11): e20516.
4. Majeed et al., Composition comprising scirpusin A and scirpusin B and anti-obesity potential thereof, U.S. Pat. No. 10,172,903.
5. Majeed et al., Method for the treatment of hypercholesterolemia, U.S. Pat. No. 9,610,273

However, a natural molecule and/or a combination of natural molecules that decrease triglycerides, especially in hypertriglyceridemia induced by chemotherapeutics and hyperglycemia are lacking. The present invention solves the above problem by disclosing a composition comprising oroxylin A, baicalein and chrysin for management of hypertriglyceridemia associated with hyperglycemia and chemotherapy.

It is a principle objective of the invention to disclose a method for therapeutic management of hypertriglyceridemia using a composition comprising oroxylin A, baicalein and chrysin.

The invention fulfils the above mentioned objective and provides further related advantages.

SUMMARY OF THE INVENTION

The present invention discloses a composition comprising not less than 10% w/w of oroxylin A, not less than 10% w/w of baicalein and not less than 2% w/w of chrysin for use in the therapeutic management of hypertriglyceridemia. More specifically, the invention discloses the use of a composition comprising not less than 10% w/w of oroxylin A, not less than 10% w/w of baicalein and not less than 2% w/w of chrysin for use in the therapeutic management of hypertriglyceridemia associated with chemotherapy and hyperglycemia.

DESCRIPTION OF THE MOST PREFERRED EMBODIMENTS

In the most preferred embodiment the invention discloses a method of therapeutic management of hypertriglyceridemia in mammals, said method comprising steps of administering effective concentration of a composition comprising not less than 10% w/w of oroxylin A, not less than 10% w/w of baicalein and not less than 2% w/w of chrysin, to mammals in need of such therapeutic management. In a related embodiment, the composition preferably comprises 10%-15% w/w of oroxylin A, 10%-25% w/w of baicalein and 2%-10% w/w of chrysin. In a related embodiment, hypertriglyceridemia is caused by chemotherapeutics and hyperglycemia. In a preferred embodiment, the mammal is human. In another preferred embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

In another preferred embodiment, the invention discloses a composition comprising not less than 10% w/w of oroxylin A, not less than 10% w/w of baicalein and not less than 2% w/w of chrysin, for use in the therapeutic management of hypertriglyceridemia in mammals. In a related embodiment, the composition preferably comprises 10%-15% w/w of oroxylin A, 10%-25% w/w of baicalein and 2%-10% w/w of chrysin. In a related embodiment, hypertriglyceridemia is caused by chemotherapeutics and hyperglycemia. In another preferred embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables. In another related embodiment, the mammal is human The specific examples included herein below illustrate the aforesaid most preferred embodiments of the present invention.

Example 1

Hypotriglyceridemic Effects of Oroxylin A, Baicalein and Chrysin (OBC) on Chemotherapy Induced Memory Impairment The composition comprising oroxylin A, baicalein and chrysin (OBC), was isolated from *Oroxylum indicum* as per the process mentioned in U.S. patent application Ser. No. 15/805,320.

Methodology: Mice received intraperitoneal (IP) injection of saline or chemotherapeutics (CT)—doxorubicin-2 mg/kg & cyclophosphamide-50 mg/kg one injection/week for 4 weeks. The composition comprising oroxylin A, baicalein and chrysin [250 mg/kg—low dose (LD) and 500 mg/kg—high dose (HD)] was mixed with powdered rodent food and fed daily for 4 weeks.

The mice serum samples were tested using an automated machine for the determination of hematological markers and other parameters to monitor liver and kidney functions.

TABLE 1

Hematological markers

| Parameters | Control | CT | CT + OBC (LD) | CT + OBC (HD) |
|---|---|---|---|---|
| Glucose | 165.00 ± 6.59 | 157.33 ± 3.59 | 202.33 ± 1.03 | 178 ± 0.44 |
| Cholesterol | 126.00 ± 1.79 | 126.66 ± 2.46 | 118 ± 1.18 | 115.33 ± 0.68 |
| Triglyceride | 166.33 ± 1.37 | 179.67 ± 2.29* | 142.67 ± 2.62 | 137.67 ± 1.81 |

*Indicates significant change $p < 0.05$

Chemotherapeutics significantly elevated triglyceride levels and OBC prevented chemotherapeutics effect. OBC may protect from drug-induced elevation of triglyceride levels.

Example 2

Effects of Composition Comprising Oroxylin A, Baicalein and Chrysin (OBC) on Hyperglycemia Induced Triglyceride Elevation The composition comprising oroxylin A, baicalein and chrysin (OBC), was isolated from *Oroxylum indicum* as per the process mentioned in U.S. patent application Ser. No. 15/805,320.

Methodology: Rats received intraperitoneal (IP) injection of saline or streptozotocin (STZ) (55 mg/kg). The composition comprising oroxylin A, baicalein and chrysin (OBC) [250 mg/kg—low dose (LD) and 500 mg/kg—high dose (HD)] was mixed with powdered rodent food and fed daily for 4 weeks.

Blood samples were withdrawn from the rats before euthanization. These samples were immediately tested using an automated machine for the determination of hematological markers and other parameters to monitor liver and kidney functions.

TABLE 2

Hematological Markers

| Parameters | Control | STZ | STZ + OBC (LD) | STZ + OBC (HD) |
|---|---|---|---|---|
| Glucose | 190.4 ± 4.56 | 602.4 ± 48.79* | 509 ± 57.53 | 561.8 ± 29.91 |
| Cholesterol | 121.8 ± 3.07 | 141.6 ± 10.48 | 130.6 ± 8.22 | 151 ± 6.98 |
| Triglyceride | 129.8 ± 5.43 | 633.2 ± 156.9* | 334.2 ± 88.11 | 551.2 ± 65.05 |

*represent significant change $p < 0.05$

OBC significantly decreases the STZ-increased triglyceride levels. These results suggest that OBC may be useful in the management of blood triglyceride levels.

In conclusion, the composition comprising oroxylin A, baicalein and chrysin was very effective in ameliorating the symptoms of chemotherapy and hyperglycemia induced triglyceride elevation. U.S. patent application Ser. No. 16/009,490 and PCT application no. PCT/US18/37724 discloses the use of comprising oroxylin A, baicalein and chrysin in ameliorating the symptoms of chemotherapy and hyperglycemia induced cognitive dysfunction and memory impairment. A large body of evidence indicate that the enzyme monoamine oxidase (MAO) play an important role in neuroprotection. However, the exact mechanisms underlying the protective effects of MAOs in the brain are still unknown. Although reports indicate that over expression of MAOs in neurodegenerative diseases like Alzheimer's disease, Parkinson's disease and epileptic seizures, deficiency of the enzyme is also reported in the above mentioned conditions. The treatment methods that are generally employed are aimed at inhibiting the activity of MAOs and bioactive molecules that increase the activity of MAOs for ameliorating the symptoms are lacking. The composition comprising oroxylin A, baicalein and chrysin may also be very effective in modulating the levels of MAOs, which can be used for the management of many neurological diseases, specifically epilepsy.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of therapeutic management of hypertriglyceridemia in mammals, said method comprising steps of administering effective concentration of a composition comprising not less than 10% w/w of oroxylin A, not less than 10% w/w of baicalein and not less than 2% w/w of chrysin to mammals in need of such therapeutic management.

2. The method as in claim 1, wherein the composition comprises 10%-15% w/w of oroxylin A, 10%-25% w/w of baicalein and 2%-10% w/w of chrysin.

3. The method as in claim 1, wherein hypertriglyceridemia is caused by chemotherapeutics and hyperglycemia.

4. The method as in claim 1, wherein the mammal is human.

* * * * *